United States Patent
Bastia et al.

(10) Patent No.: US 7,452,329 B2
(45) Date of Patent: Nov. 18, 2008

(54) RETRACTOR FOR OPERATIONS ON THE ARTERIA HAEMORROIDALIS

(75) Inventors: Filippo Bastia, Carpi (IT); Carlo Tagariello, Bologna (IT); Pier Paolo Dal Monte, Pianoro (IT)

(73) Assignee: THD S.p.A., Correggio (IT)

( * ) Notice: Subject to any disclaimer, the term of this patent is extended or adjusted under 35 U.S.C. 154(b) by 130 days.

(21) Appl. No.: 10/540,764

(22) PCT Filed: Jan. 21, 2003

(86) PCT No.: PCT/EP03/00543

§ 371 (c)(1),
(2), (4) Date: Nov. 14, 2005

(87) PCT Pub. No.: WO2004/064624

PCT Pub. Date: Aug. 5, 2004

(65) Prior Publication Data

US 2006/0155169 A1    Jul. 13, 2006

(51) Int. Cl.
*A61B 1/00*    (2006.01)
(52) U.S. Cl. .................. 600/184; 600/105; 600/199; 600/201; 600/220; 600/221; 600/222; 600/223; 600/129; 606/110; 606/111; 606/112; 606/113; 606/197; 606/205; 606/206; 606/207
(58) Field of Classification Search .............. 600/184, 600/201, 223, 245–246
See application file for complete search history.

(56) References Cited

U.S. PATENT DOCUMENTS

| 348,843 A | * | 9/1886 | Hamilton ............... 600/184 |
| 2,482,971 A | | 9/1949 | Kendall | |
| 3,701,347 A | * | 10/1972 | Belkin ............... 600/184 |

(Continued)

FOREIGN PATENT DOCUMENTS

DE    830 544    2/1952

(Continued)

*Primary Examiner*—Linda C. M. Dvorak
*Assistant Examiner*—Matthew J Kasztejna
(74) *Attorney, Agent, or Firm*—Pearne & Gordon LLP

(57) ABSTRACT

The invention describes a disposable device for operations on the arteria haemorroidalis, which comprises a retractor tube (1), closed and rounded on the end (101) which is inserted in the anal cavity, and open and diverging on the external end (201) to which is connected a griping handle (M) which removable houses a luminous source (F). In the connection zone of the handle to the external mouth of the retractor there is provided a channel (C) which contains a parabola (5) which reflects the light supplied from said luminous source (F) and which sends the reflected light inside of the same retractor, to illuminate a lateral window (8) through which appears the rectal mucosa upon which the operation must be made for the ligature of the arteria haemorroidalis. The haematic flow of the arteria haemorroidalis and the same artery are detected with precision by means of an ultrasonic probe removably housed in a longitudinal chamber (10) provided at the interior of the retractor tube, aligned to said window (8), opened on the mouth (201) of the same retractor and also provided with a lateral opening (7) to allow to the sensor of the probe to touch the anal mucosa. The probe is preferably protected in a thin, disposable and easily removable sterilised sheath, to allow the hygienical re-utilization of the same probe.

25 Claims, 4 Drawing Sheets

U.S. PATENT DOCUMENTS

| | | | |
|---|---|---|---|
| 4,527,553 A * | 7/1985 | Upsher | 600/188 |
| 4,641,663 A | 2/1987 | Juhn | |
| 4,766,886 A | 8/1988 | Juhn | |
| 4,819,620 A * | 4/1989 | Okutsu | 600/114 |
| 5,570,692 A | 11/1996 | Morinaga | |
| 6,390,973 B1 | 5/2002 | Ouchi | |
| 6,595,917 B2 * | 7/2003 | Nieto | 600/223 |
| 6,616,603 B1 | 9/2003 | Fontana | |

FOREIGN PATENT DOCUMENTS

| | | |
|---|---|---|
| DE | 199 29 314 A1 | 12/1999 |
| EP | 1 234 539 A2 | 8/2002 |
| EP | 1234539 A2 | 8/2002 |
| FR | 2 623 078 | 5/1989 |

\* cited by examiner

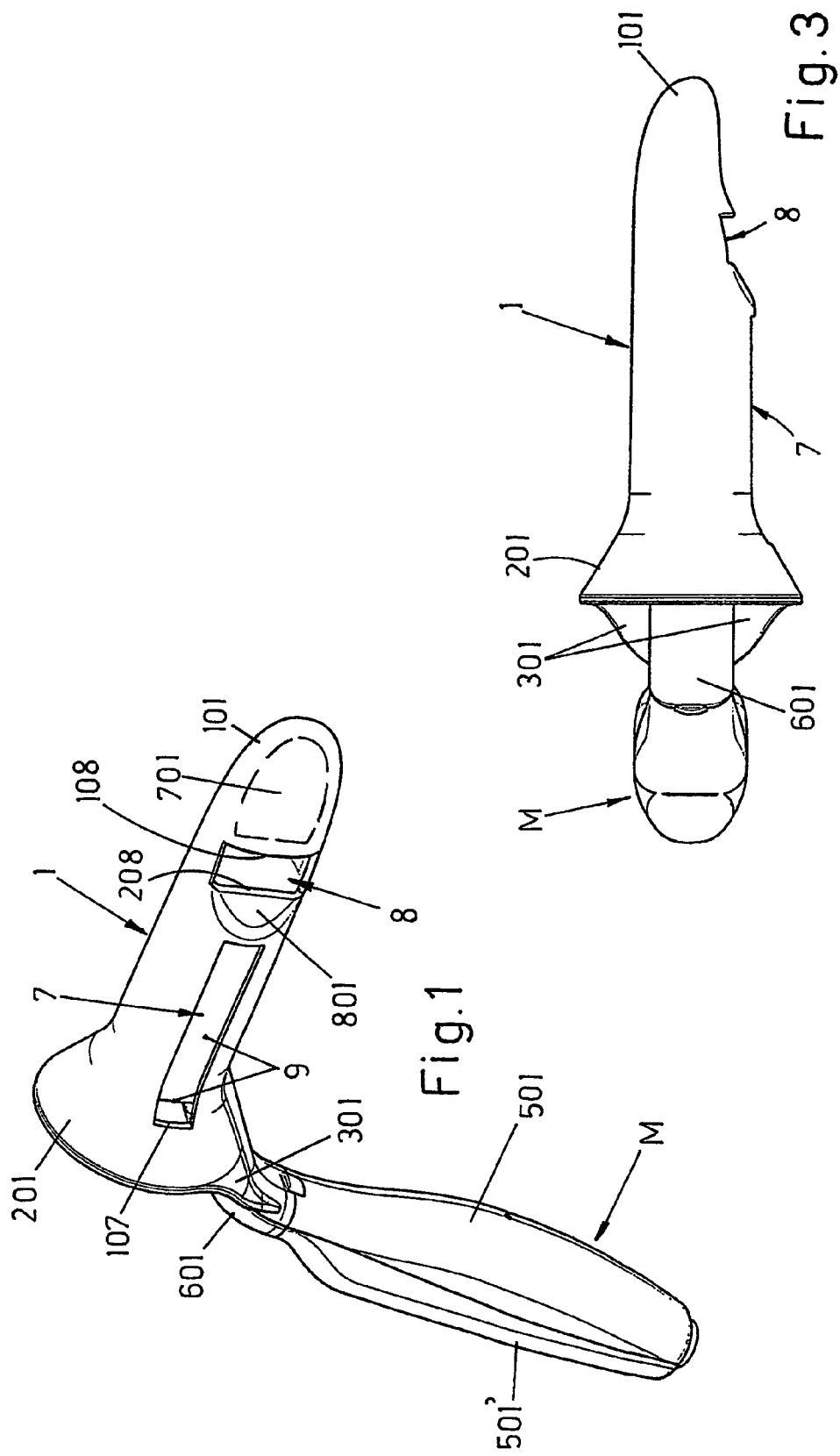

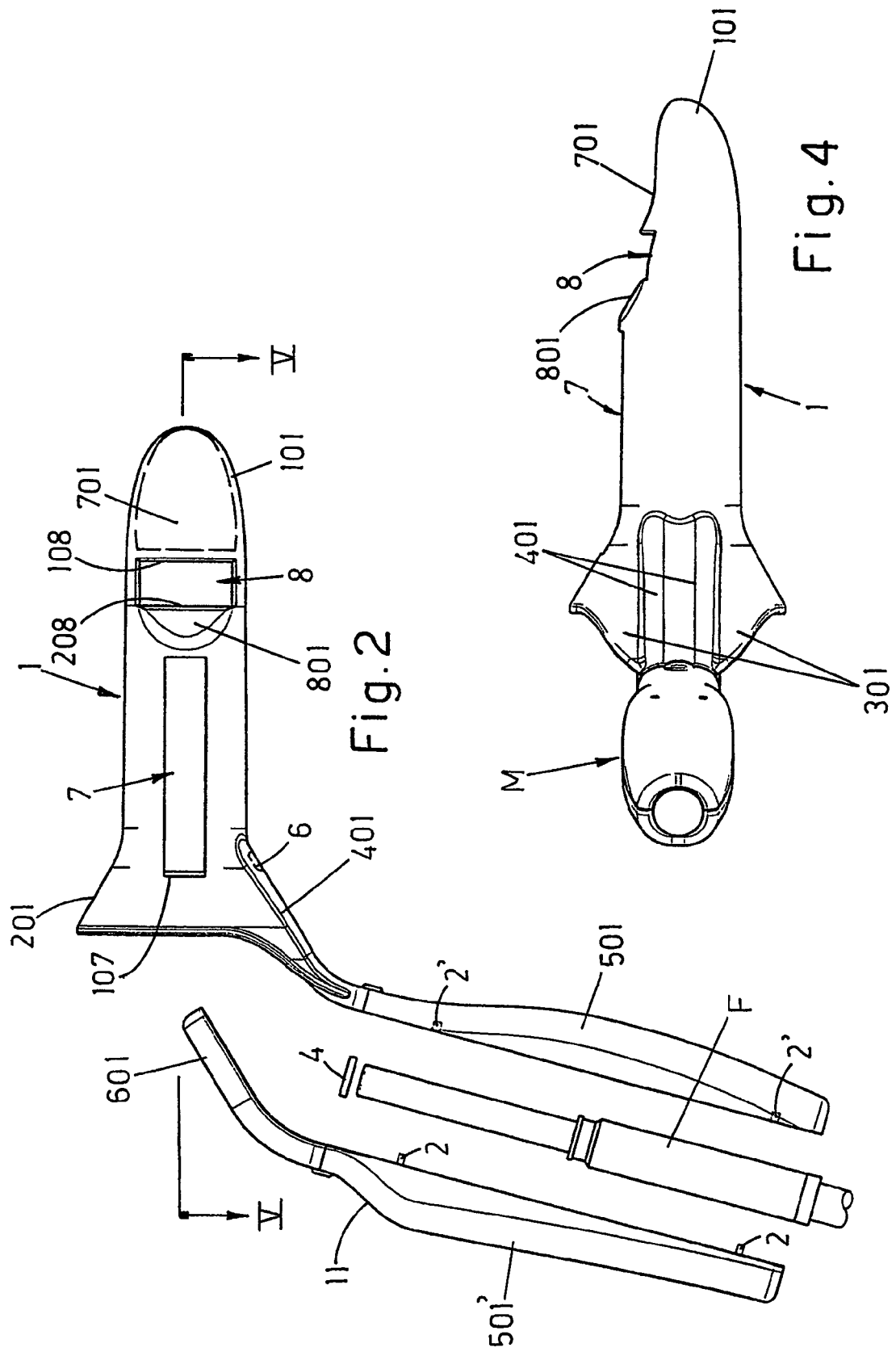

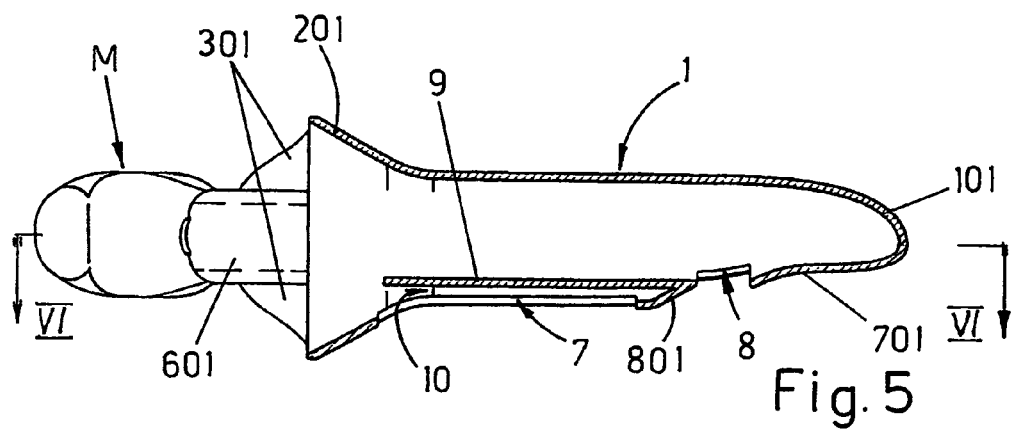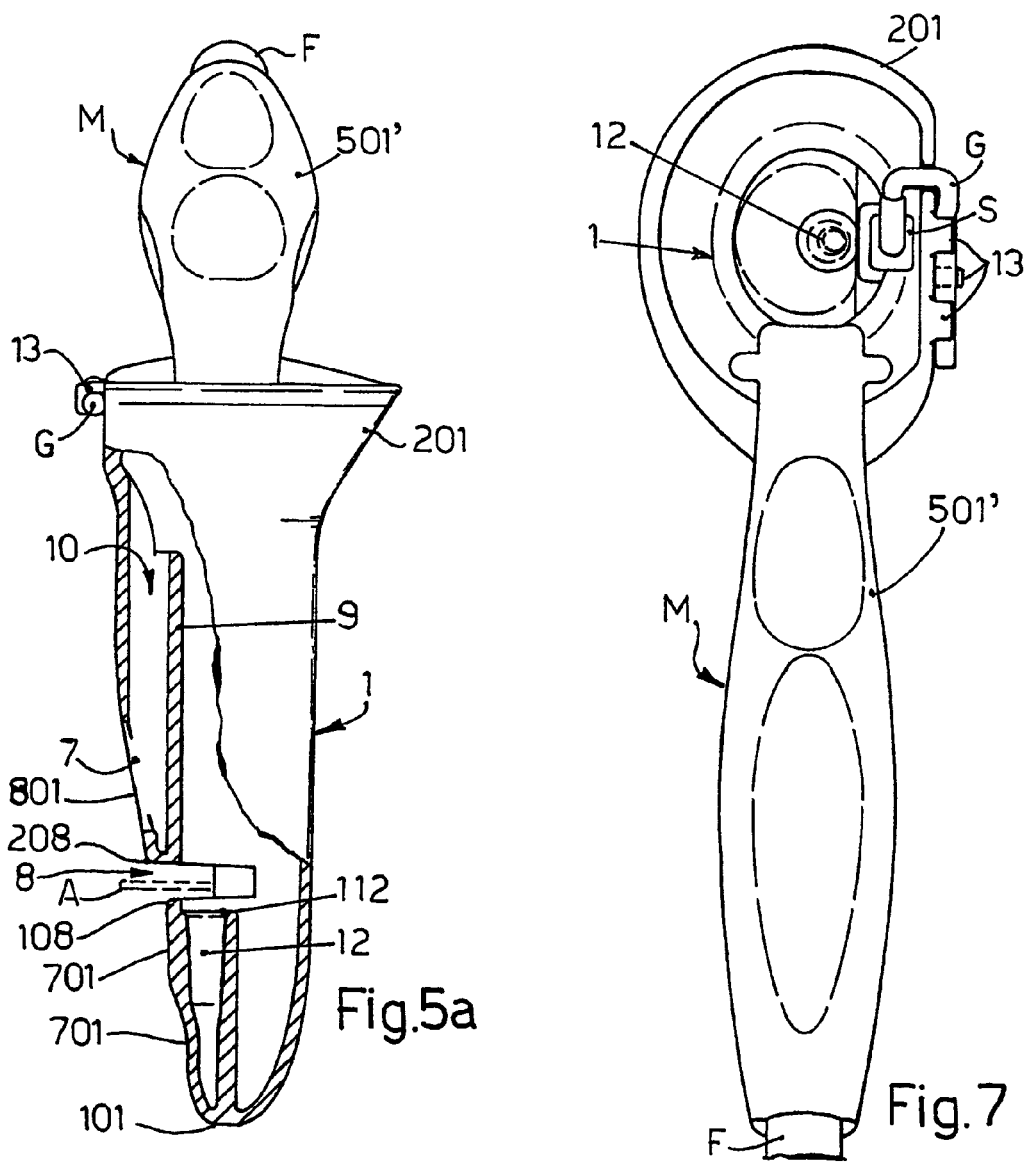

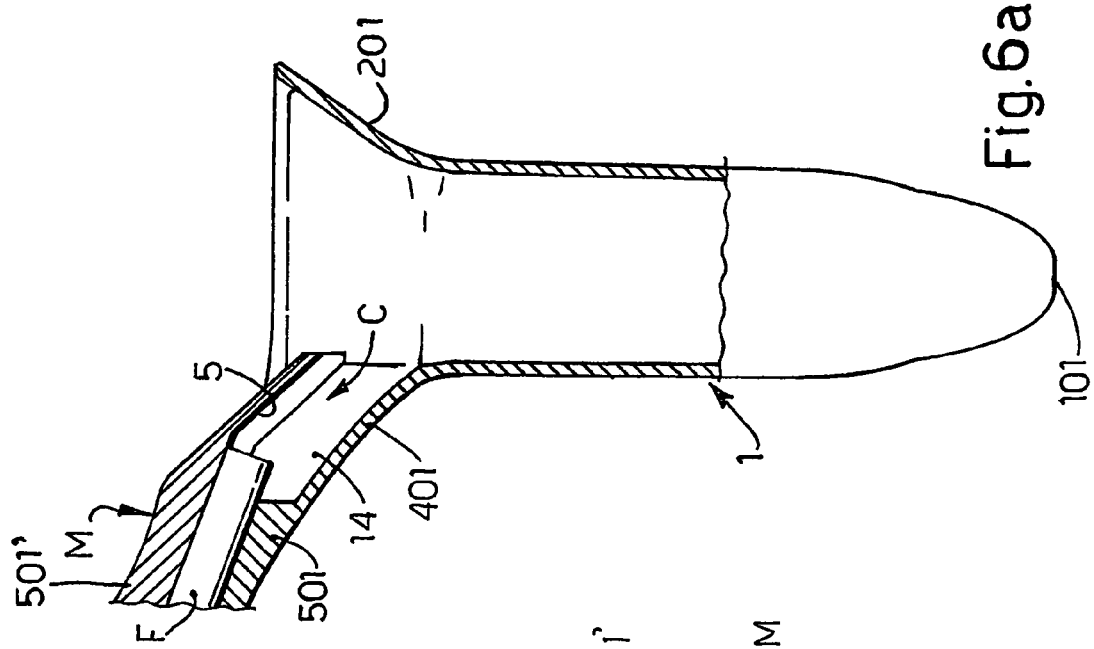
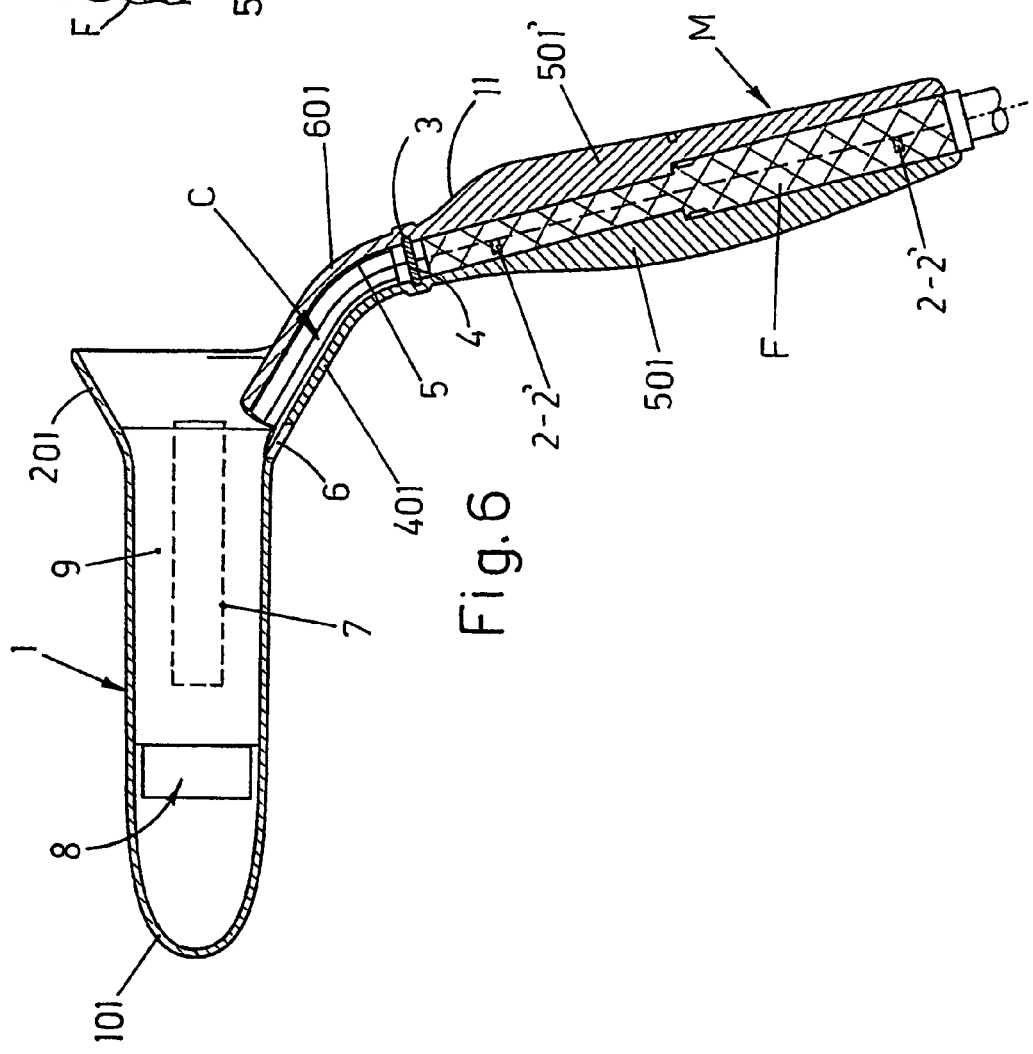

RETRACTOR FOR OPERATIONS ON THE ARTERIA HAEMORROIDALIS

In order to effect ambulatory operations on the haemorrhoids, without anaesthesia, it is known the use of the device described in the U.S. Pat. No. 5,570,692, which comprises a retractor tube closed on the end which is inserted in the anal cavity and opened on the external end, which is provided with a gripping handle. The retractor tube is provided on its lateral wall, at a short distance from its closed end, with an ultrasonic probe to detect the blood flow of the haemorrhoidalis artery and is provided near to the probe, with a lateral window through which may be detected and observed the portion of the anal mucosa upon which it must be operated for the ligature of said artery, for example by means of a curved needle or by means of cauterisation. The closed end of the retractor tube, may be illuminated by a luminous source housed in said end and connected to feeding means provided in the handle, together with the feeding means of said probe. This device, for the reason that incorporates the ultrasound probe and that houses the luminous source in its closed end, presents elevated production costs, so that it is not possible to propose the same as a disposable product, with all the drawbacks and the limitations deriving by this fact.

Object of the invention is to obviate to these and other limits of the known prior art, with a disposable device, for the realisation of which it has been necessary to resolve some technical problems connected with the removable housing in the same of the ultrasonic probe and other problems related to the means for the illumination of the lateral window for the exploration of the anal mucosa. The first of said problems has been solved providing in the retractor tube a longitudinal seat, closed toward the interior and opened with the end toward the outer end of the same tube, in which seat it is possible to removably house an ultrasonic probe which partially projects through a longitudinal opening of the retractor tube, to result in contact with the anal mucosa. The ultrasonic probe is preferably inserted and hygienically protected in a sterile, disposable and easily removable sheath, having a suitable conformation, in such a manner that the same may be reutilized repeatedly in other disposable devices of the type which is referred to. Immediately downstream of the seat with the ultrasonic probe, there is provided the window for the exploration of the anal mucosa. To solve the problem of the illumination, it has been used the technique of the back illumination, known in the proctoscopies, which provides the movable insertion of a luminous source in the handle of the device. Instead of the use of curved light guide means, realised for example with optical fibre or with a bar of plastics, connected with one of their end to said luminous source and oriented with the other end in the field of view defined by the internal cavity of the retractor tube, as described for example in the Italian patent No. 1 234 169, in the device according to the invention are utilised curved means to reflect the light inside of the retractor tube, with the advantage of a better luminous yield and with the advantage that such devices result distant from the internal surface of the same retractor and can not be soiled and blinded by the physiological liquid which unavoidably is produced by the anal cavity during the operation which is referred to.

These and other features of the invention, and the advantages deriving therefrom, will appear better evident from the following description of a preferred embodiment of the same, made by way of non-limiting example, with reference to the figures of the attached sheets of drawings, in which:

FIG. 1 is a perspective view of the device without the ultrasonic probe and without the illumination source;

FIG. 2 shows the device in lateral elevation, decomposed in the pieces which compose it and with the illumination source placed between the two portion of the handle in which the same is inserted;

FIGS. 3 and 4 show the device respectively in plan view from above and in plan view from the bottom;

FIG. 5 shows the device assembled and sectioned along the line V-V of FIG. 2;

FIG. 6 shows further details of the device sectioned along the line VI-VI of FIG. 5;

FIGS. 5*a* and 6*a* show embodiments of the device respectively viewed as in the preceding FIGS. 5 and 6;

FIG. 7 shows the device of the FIG. 5*a* according to a view of the front toward the operator.

From the Figures it is noted that the device comprises a substantially cylindrical tube 1 having the function of retractor, closed at its terminal end 101 which is opportunely tapered and rounded, and on the contrary open on the initial end 201 which has a conical shape and which is outwardly divergent. Merely by way of example, the body 1 may have an external diameter which is comprised between 2,5 and 3,5 centimeters, for example of about 3 centimeters, an may have a general length comprised between 10 and 12 centimeters, comprehensive of the divergent end 201 which has alone the length of about 2 centimeters. However, it is to be understood that the device may be realised with dimensions which are different to the indicated dimensions, in order to comply with different use requirements. The conical end 201 is outwardly projecting with a portion having a substantially triangular plan 301, having a length of some centimeters, provided in its center line with a longitudinal and channel-shaped rib 401, outwardly convex, which has prevalently the function to increase the resistance to the bending and torsion stress of said appendices 301 and to partially define the duct along which will be effected the reflection of the light for the illumination of the working zone. The appendix 301, which has for example an inclination of about 30° with respect to the longitudinal axis of the body 1, integrally connects to said body an elongated shell 501 realised with a suitable ergonomic shape for the function of gripping handle, having for example a length of about 10 centimeters and which is forming with the axis of said body 1 an internal angle of about 105°. It is to be understood that also these last dimension data of the device are merely indicative and that the same may be widely modified. The connecting zone of the shell 501 to the appendices 301, is suitably curved. Upon the shell 501 there is placed and fixed with the male-female fixed coupling portions 2, 2', a complementary shell 501' which completes the formation of the gripping handle M and which is superimposed to the ribbed portion 401 of the appendix 301, with a terminal portion 601 having the shape of a channel, which is connected to the same shell 501' with a suitable curvature, which ends in the connecting zone of the conical portion 201 to the cylindrical portion of the tube 1 and then in the internal portion of said tube which appears through the same conic mouth 201. The portion 601 realises with the portion 401 a tubular duct C which at least from the outside presents a flat shape also for the presence of lateral ribs, in such a manner to result with high features of resistance to the bending and to the torsion. In the conjunction zone of the shell 501 to the channel 601, there is provided a step 11 raised toward said shell, suitable for leaning the thumb of the hand which grasps the handle M, to ensure a steady grasp of the same handle and to facilitate in absolute the use of the device.

In the conjunction zone of the unit of the handle M to the appendix 301, inside of the two complementary shells which define the same handle, are obtained the two complementary portions of an annular seat 3 in which can be placed a small disk 4 made of transparent material, which realises a division barrier between the internal and absolutely sterile portion of the instrument, from the internal and hollow portion of the handle, in which is inserted and retained for example by means of friction, the end of the illumination optical waveguide F, of the known type, which may be not subjected to sterilisation treatments. The small disk 4 may have, if required, optical functions and may be made by means of a lens suitable to focalise the light on a reflection parabola 5 which covers the internal surface of the portion 601 of the duct C and which can be, for example, realised in a very economical and reliable manner, with an electrochemical metal spray coating of chrome. The advantages deriving from the backlight system described, with respect to the known systems which use light guides, are represented by a better luminous efficiency and especially by the fact that the same illumination means may be not blinded by the organic liquid which can come out from the hollow of the retractor tube, because the reflection parabola 5 remains raised from the path of said liquid, and because also in the most unfavourable condition shown in FIG. 6, it is possible to foresee upstream of the small disk 3, on the ribbed zone 401, one or more drainage openings 6, suitably shaped, through which said organic liquid may freely come out. The device is preferably realised with plastics of a changing white colour, to exalt the effects of the illumination inside the body 1. From the drawings, it appears that the retractor tube 1 is laterally provided with a longitudinal and rectilinear opening 7, for example with a rectangular shape, which begins in the zone in which the end conic portion 201 is connected to the cylindrical portion of the same retractor 1 and which has a length which is about equal to the half length of the same retractor. In the example which is referred to, the ideal plane in which lies the opening 7 is parallel to the center line plane of the device and the same opening is placed on the right side of the body 1 if the device is considered with the handle M downwardly oriented, but it is to be understood that said collocation may be diversified. It is not even excluded that the ideal plane on which the opening 7 lies, may be differently perpendicular to the vertical center line plane of the device, with the same window which results placed in the upper portion of the body 1 if the device is considered with the handle downwardly oriented, also to cause the terminal and internal portion of the body retractor, placed downstream of the zone interested by said opening, may be better illuminated by the beam which comes out from the reflection parabola 5. In fact, in said zone, the retractor body 1 presents a tapered and slightly flattened shape, as shown with numeral reference 701, in the initial portion of which is provided, transversally oriented with the greatest dimension, a window 8 for example with a rectangular shape, for example having the dimensions of centimeters 1×2, through which it will appears the anal mucosa which will be efficaciously illuminated by the above mentioned backlight means. The window 8 is distant from the outer end of the body 1, which is connected to the conical portion 201, of about 4-7 centimeters, for example of about 5-6 centimeters. In the zone which is comprised between the rear edge 208 of the window 8 and the rear side 107 of the openings 7, the body 1 presents internally and integral a flat division wall 9, which delimits inside the same body 1 a longitudinal chamber 10 open on the end toward the mouth 201 of the retractor and provided with the outer and lateral opening 7 above mentioned. In said chamber 10 is friction inserted a ultrasound probe, not illustrated, which will be realised with such shape to opportunely project from the opening 7, to result in contact with the rectal mucosa. As said in the introduction of the present description, the probe may be contained in a thin sterilised, disposable and easily removable sheath, so that the same probe may be used several times in other disposable devices of the type which is referred to. The connection cable to the probe, will go out from the mouth 201 of the retractor and it may be temporarily fixed with an adhesive bandage on a side of the handle M. It is to be understood that the handle M and other portions of the device (see further) may be laterally provided with small loops having the shape of pincers, integral obtained upon the shells 501, 501' and suitable to temporarily support the cable of the ultrasound probe above mentioned. As appears from FIGS. 3-5, the window 8 lies on a terminal portion of the retractor tube which is slightly flattened and in recess and the rear side 208 of said window is connected with an inclined plane 801 with the lateral surface of the retractor. The forward edge 108 of the window 8 is then characterised by the fact that it is in relief and to have a slightly arcuate shape, with the convexity turned toward the outside. All these conditions allow to optimise the dilatation of the rectal tissues and contextually to avoid prolapse of the same inside the window 8, in such a manner that through said window the rectal mucosa presents itself in the better condition to operate on the same with the known and required means for the ligature of the arteria haemorrhoidalis, which can be identified with precision by means of the said ultrasonic probe.

The device shown in FIGS. 5a, 6a and 7 is different from the device previously described for the several features below considered. The window 8 is, for example, arcuate-shaped, is obtained on the retractor tube 1 substantially for half of its circumference, and has a length which is inferior to 1 centimeter, for example comprises between 8 and 5 millimeters. The inclined plane 801, placed immediately downstream of the window 8, is more wide and less inclined of that of the Figures from 1 to 5, and upon it there is localised the opening 7 which exposes the sensible portion of the ultrasonic probe S visible in FIG. 7, in such a manner that this same portion results very close to the said window 8 and to the portion of the arteria haemorroidalis upon which the operation will be made.

The forward side 108 of the window 8 it is not in relief as in the previous solution, but it is lower with respect to the posterior side 208 of the same window and forms part of a flat portion 701' which is substantially aligned to the wall 9 for the delimitation of the chamber 10 housing the probe S, said portion being connected with a correct union to the remaining flat portion 701, in such a manner to form in the whole a flat portion with a sinuous profile and with a decreasing profile toward the rounded point 101.

Always from FIG. 5a it appears that under the portions 701, 701' above mentioned, inside the body 1 is obtained a seat 12 having for example a rounded section and a conic shape, with a superior edge 112 slightly placed beyond the anterior edge 108 of the window 8, in such a manner to rest upon said edge and to insert in said seat, the terminal portion of a mandrel not shown, which holds the curved needle A with which will be made the ligature of the arteria haemorroidalis and that with the external end of the retractor tube 1 may be easily operated by the operator. The axis of the seat 12 is for example parallel and suitably displaced from the axis of the retractor tube 1.

From FIGS. 5a and 7 it is noted that the initial conic portion 201 of the retractor 1, is flattened on the side corresponding to the seat 10 for the housing of the probe S and on this side it carries a set of three appendices 13 upon which it is possible to firmly anchor the portion of the cable G which is near to the same probe.

From FIG. 6 it is finally noted that the reflecting portion 5 is placed only in the terminal and rectilinear portion of the channel C, with an inclination of about 40-45° with respect to the longitudinal axis of the retractor 1, for example of about 43°. The terminal portion of the optical waveguide F for the illumination is now placed at a short distance from the reflecting surface 5, in such a manner to sensibly improve the illumination intensity of the internal cavity of the same retractor. The longitudinal axis of the terminal portion of the optical waveguide F inserted in the handle M, forms with the axis of the retractor 1 an internal angle of about 110°. Always from FIG. 6a it is finally noted how the same terminal portion of the optical waveguide F results raised from the bottom of the channel C with the reflecting surface 5, for the presence of the wide recessed portion 14 in the conjunction zone 401 of the handle M to the retractor tube 1, zone which may be provided with, if required, said drainage opening/s.

The invention claimed is:

1. Disposable device for surgical operation on the hemorrhoidal artery, comprising:
   a retractor tube, closed and rounded at one end which is insertable into an anal orifice, the retractor tube being provided upon its side surface with at least an exploration window through which a rectal mucosa can be observed, the retractor tube being also provided with a gripping handle, integral with an external mouth of the retractor tube, through said external mouth being possible to observe said rectal mucosa and to insert in the retractor tube instruments required for the surgical operation;
   a luminous source fixed in removable manner inside the gripping handle, for illuminating said window and the rectal mucosa which appears through the window;
   means for reflecting the light supplied from said luminous source and for allowing said reflected light to illuminate the internal portion of the retractor tube and said window, said light reflecting means being located at the level of a conjunction zone of the gripping handle to the external mouth of the retractor tube;
   the retractor tube being provided, in alignment with the exploration window and upstream of said exploration window, with a longitudinal, internal chamber at least partially defined by a wall which is integral with internal walls of the retractor tube and with a posterior side of the exploration window, so that the chamber has an opening toward the external mouth of the retractor tube; the device also comprising an ultrasonic probe, friction-housed in said chamber and at least partially exposed through an opening longitudinally obtained on a lateral wall of the retractor tube, so that said probe is able to enter in contact with the rectal mucosa.

2. Device according to claim 1, wherein the reflecting means comprise a specular reflection parabola which is placed longitudinally and in a portion raised from the bottom of a tubular channel which connects a hollow portion of the handle with the external mouth of the retractor tube, the specular reflection parabola terminating at the interior of said retractor tube.

3. Device according to claim 2, wherein said tubular channel has at least externally a flat configuration with reinforcements at the sides, in such a manner to increase resistance of the channel to bending and torsion.

4. Device according to claim 2, wherein at least a top portion of the channel which houses the reflection parabola is affixed and fixed upon another portion of the same channel for simplifying the realization and/or the installation of said reflection parabola.

5. Device according to claim 4, wherein the reflection parabola is obtained by an electrochemical process of chromium plating of an internal surface of the top and affixed portion of the channel.

6. Device according to claim 4, wherein the top and affixed portion of the channel having the reflection parabola is integrally obtained with an upper shell-shaped portion of the gripping handle, said upper shell-shaped portion being designed to be coupled with a lower shell-shaped complementary portion for completing the handle, said lower shell-shaped complementary portion being integral with a longitudinally ribbed and outwardly convex portion of the handle which forms a lower portion of the same channel and which is obtained in an appendix of the retractor tube having a substantially triangular plan, said appendix having sides which are tangent to an external edge of the external mouth of the retractor tube.

7. Device according to claim 6, wherein a connecting zone between said top portion of the channel having the reflection parabola and the upper shell-shaped portion of the gripping handle presents a step raised toward the handle, the step being designed to be engaged by a thumb of a hand of an operator which grasps the same handle so that the thumb can lean on said step, in such a way to ensure a steady grasp and an easy use of the device.

8. Device according to claim 6, wherein in connecting portions between the upper and lower shell-shaped portions and the portions of the channel which contain the reflection parabola are obtained complementary portions for the formation of a seat in which a disk of transparent material can be housed, said disk being able to divide in a tight manner the channel from a seat of the handle in which is removably housed the luminous source.

9. Device according to claim 8, wherein the transparent small disk is made by a lens which focalizes on the reflection parabola the light which is supplied by the luminous source.

10. Device according to claim 6, wherein on a lower portion of the channel having the reflection parabola is provided with at least one opening for outwardly discharging organic liquids which come by gravity to said opening and to avoid that such liquids arrive on said disk placed upwardly of the luminous source.

11. Device according to claim 2, wherein the channel having the reflection parabola presents an inclination comprised between 30 DEG and 50 DEG with respect to a longitudinal axis of the retractor tube, and wherein the handle presents an inclination comprised between 100 DEG and 120 DEG with respect to said longitudinal axis of the retractor tube.

12. Device according to claim 2, wherein the device is formed with a plastic of changing white color, for facilitating an internal illumination of the retractor tube and of said exploration window.

13. Device according to claim 2, wherein the channel having the reflection parabola presents a recess zone which leaves uncovered an end portion of the luminous source which is placed at a short distance from said reflection parabola.

14. Device according to claim 1, wherein the exploration window lies on a plane which is substantially parallel to a center line plane of the device and is placed on a side of the retractor tube with respect to a configuration wherein the handle is oriented downwardly.

15. Device according to claim 1, wherein the exploration window lies on a plane which is substantially perpendicular to a center line plane of the device and is placed upwardly with respect to a configuration wherein the handle is oriented downwardly.

16. Device according to claim 1, wherein the exploration window has a distance from the end of the retractor tube which is connected to the external mouth which is comprised between 4 and 7 centimeters.

17. Device according to claim 1, wherein the exploration window lies on a flattened and slightly recessed portion of the lateral wall of the retractor tube which is near to the rounded and closed end of the retractor tube, a rear side of the exploration window being rounded and connected with the lateral surface of said tube by means of an inclined plane, a forward side of the exploration window being rounded and raised and presenting an arcuate shape, for better dispose the anal tissue to the exploration and to the operation through the exploration window.

18. Device according to claim 1, wherein the exploration window is transversally obtained on the retractor tube and intersects the retractor tube for about a half of its circumference, a rear side of said exploration window being rounded and connected by means of a wide inclined plane with the lateral surface of said tube, a forward side of the exploration window being rounded too, being lowered with respect to said rear side of the exploration window and being connected to flat portions which extend with a sinuous shape and with a decreasing profile toward the rounded closed end of the retractor tube.

19. Device according to claim 1, wherein said device comprises receiving and centering means for receiving and rotatably centering one end of a mandrel which carries a curved needle for the ligature of the haemorrhoidal artery, said receiving and centering means being located inside of the retractor tube under the exploration window, at a short distance from the exploration window and at the level of a center line of said exploration window.

20. Device according to claim 19, wherein said receiving and centering means comprise a rounded section seat, placed parallel to a longitudinal axis of the retractor tube and with a distance from said longitudinal axis of the retractor tube.

21. Device according to claim 20, wherein said rounded section seat has a conical shape and gets narrower toward the rounded closed end of the retractor tube.

22. Device according to claim 1, wherein said opening, through which the ultrasonic probe is at least partially exposed, abuts an inclined portion which converges on a posterior wall of the exploration window.

23. Device according to claim 1, wherein the ultrasonic probe is hygienically protected in a sterile, disposable and easily removable sheath, for allowing hygienic re-utilization of the same probe.

24. Device according to claim 1, wherein a side of the external mouth of the retractor tube is flattened on the side of the chamber for the housing of the ultrasonic probe and carries appendices designed to removably anchor a cable of the ultrasonic probe.

25. Device according to claim 24, wherein the handle is provided, on the side near to the ultrasonic probe, with appendices designed to removably anchor a further portion of said cable of the ultrasonic probe.

* * * * *